(12) United States Patent
Nelson

US007786099B2

(10) Patent No.: US 7,786,099 B2
(45) Date of Patent: Aug. 31, 2010

(54) AROMATIC A-RING DERIVATIVES OF TETRACYCLINE COMPOUNDS

(75) Inventor: Mark L. Nelson, Norfolk, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1428 days.

(21) Appl. No.: 11/039,230

(22) Filed: Jan. 18, 2005

(65) Prior Publication Data

US 2006/0003971 A1 Jan. 5, 2006

Related U.S. Application Data

(60) Provisional application No. 60/537,228, filed on Jan. 15, 2004, provisional application No. 60/558,907, filed on Apr. 1, 2004, provisional application No. 60/622,720, filed on Oct. 27, 2004.

(51) Int. Cl.
*A61K 31/65* (2006.01)
*C07C 50/22* (2006.01)
*C07C 50/36* (2006.01)

(52) U.S. Cl. .................................. 514/152; 552/200
(58) Field of Classification Search ................ 552/200; 514/152
See application file for complete search history.

(56) References Cited

U.S. PATENT DOCUMENTS

| | | | |
|---|---|---|---|
| 2,980,584 A | 4/1961 | Hammer | 514/153 |
| 2,990,331 A | 6/1961 | Horst et al. | 514/619 |
| 3,043,876 A * | 7/1962 | Rennhard et al. | 552/202 |
| 3,062,717 A | 11/1962 | Hammer | 514/153 |
| 3,081,346 A * | 3/1963 | Stephens, Jr. et al. | 552/203 |
| 3,165,531 A | 1/1965 | Blackwood et al. | 549/41 |
| 3,239,499 A | 3/1966 | Rennhard et al. | 534/658 |
| 3,250,810 A | 5/1966 | Blackwood | |
| 3,304,227 A | 2/1967 | Loveless | 514/152 |
| 3,454,697 A | 7/1969 | Joyner et al. | 514/154 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 4,666,897 A | 5/1987 | Golub et al. | 514/152 |
| 4,704,383 A | 11/1987 | McNamara et al. | 514/152 |
| 4,925,833 A | 5/1990 | McNamara et al. | 514/152 |
| 4,935,412 A | 6/1990 | McNamara et al. | 514/152 |
| 5,064,821 A | 11/1991 | Levy et al. | 514/154 |
| 5,258,371 A | 11/1993 | Golub et al. | 514/152 |
| 5,308,839 A | 5/1994 | Golub et al. | 514/152 |
| 5,321,017 A | 6/1994 | Golub et al. | 514/152 |
| RE34,656 E | 7/1994 | Golub et al. | 514/152 |
| 5,326,759 A | 7/1994 | Hlavka et al. | 514/227.5 |
| 5,328,902 A | 7/1994 | Sum et al. | 514/152 |
| 5,459,135 A | 10/1995 | Golub et al. | 514/152 |
| 5,495,018 A | 2/1996 | Sum et al. | 544/63 |
| 5,495,030 A | 2/1996 | Sum et al. | 552/205 |
| 5,495,031 A | 2/1996 | Sum et al. | 552/206 |
| 5,495,032 A | 2/1996 | Sum et al. | 552/206 |
| 5,512,553 A | 4/1996 | Sum et al. | 514/152 |
| 5,523,297 A | 6/1996 | Pruzanski et al. | 514/152 |
| 5,532,227 A | 7/1996 | Golub et al. | 514/152 |
| 5,589,470 A | 12/1996 | Levy | 514/154 |
| 5,668,122 A | 9/1997 | Fife et al. | 514/152 |
| 5,675,030 A | 10/1997 | Krishnan et al. | 552/205 |
| 5,770,588 A | 6/1998 | McNamara et al. | 514/152 |
| 5,773,430 A | 6/1998 | Simon et al. | 514/152 |
| 5,789,395 A | 8/1998 | Amin et al. | 514/152 |
| 5,811,412 A | 9/1998 | Levy | 514/154 |
| 5,827,840 A | 10/1998 | Ramamurthy et al. | 514/152 |
| 5,834,450 A | 11/1998 | Su | 514/152 |
| 5,834,499 A | 11/1998 | Iwaoka et al. | 514/366 |
| 5,837,696 A | 11/1998 | Golub et al. | 514/152 |
| 5,843,925 A | 12/1998 | Backer et al. | 514/152 |
| 5,886,175 A | 3/1999 | Sum et al. | 544/63 |
| 5,919,774 A | 7/1999 | Bach et al. | 514/91 |
| 5,919,775 A | 7/1999 | Amin et al. | 514/152 |
| 5,929,055 A | 7/1999 | Ryan et al. | 514/152 |
| 5,977,091 A | 11/1999 | Nieman et al. | 514/152 |
| 5,998,390 A | 12/1999 | Ramamurthy | 514/94 |
| 6,015,804 A | 1/2000 | Golub et al. | 514/152 |
| 6,043,225 A | 3/2000 | Shor et al. | 514/29 |
| 6,043,231 A | 3/2000 | Pruzanski et al. | 514/152 |
| 6,100,248 A | 8/2000 | Golub et al. | 514/152 |
| 6,165,999 A | 12/2000 | Vu | 514/152 |

(Continued)

FOREIGN PATENT DOCUMENTS

WO    WO 95/22529    8/1995

(Continued)

OTHER PUBLICATIONS

Blackwood et al., Some transformations at the 12a-position of hte tetracyclines. Journal of teh American Chemical Soc., vol. 82, pp. 745-746, 1960.*

(Continued)

*Primary Examiner*—Barbara P Badio
(74) *Attorney, Agent, or Firm*—Mintz Levin Cohn Ferris Glovsky and Popeo, P.C.; Ivor R. Elrifi, Esq.; Heidi A. Erlacher, Esq.

(57) ABSTRACT

Aromatized A-ring derivatives of tetracycline compounds are described.

38 Claims, No Drawings

U.S. PATENT DOCUMENTS

| | | | |
|---|---|---|---|
| 6,231,894 B1 | 5/2001 | Stamler et al. | 424/718 |
| 6,277,061 B1 | 8/2001 | Golub et al. | 517/152 |
| 6,818,635 B2 | 11/2004 | Nelson et al. | 514/152 |
| 6,846,939 B2 | 1/2005 | Nelson et al. | 552/205 |
| 2004/0002481 A1 | 1/2004 | Ashley et al. | 514/152 |
| 2004/0214800 A1 | 10/2004 | Levy et al. | 514/152 |
| 2005/0288262 A1 | 12/2005 | Bandarage et al. | 514/152 |

FOREIGN PATENT DOCUMENTS

| | | |
|---|---|---|
| WO | WO 01/52858 | 7/2001 |
| WO | WO 01/74761 | 10/2001 |
| WO | WO 02/04404 | 1/2002 |
| WO | WO 02/04405 | 1/2002 |
| WO | WO 02/04406 | 1/2002 |
| WO | WO 02/04407 | 1/2002 |
| WO | WO 02/12170 | 2/2002 |
| WO | WO 02/072022 | 9/2002 |
| WO | WO 02/072031 | 9/2002 |
| WO | WO 02/072506 | 9/2002 |
| WO | WO 02/072545 | 9/2002 |
| WO | WO 02/085303 | 10/2002 |
| WO | WO 03/005971 | 1/2003 |
| WO | WO 03/057169 | 7/2003 |
| WO | WO 03/075857 | 9/2003 |
| WO | WO 03/079983 | 10/2003 |
| WO | WO 03/079984 | 10/2003 |

OTHER PUBLICATIONS

Rogalski, W., "Chemical Modification of the Tetracyclines," *The Tetracyclines*, Springer-Verlag, J.J. Hlavka and J.J. Boothe eds., Chapter 5, pp. 179-182.

McCormick, J.R.D., et al., "Biosynthesis of Tetracyclines. XI. The Methylanthrone Analog of Protetrone," *Journal of the American Chemical Society*, vol. 90(25):7127-7129 (1968).

International Search Report Application No. PCT/US2005/004793, dated Jun. 21, 2005.

Berge et al., "Pharmaceutical Salts", *J. Pharm. Sci.*, 66(1):1-19 (1977).

Chandler et al., "Matrix metalloproteinases, tumor necrosis factor and multiple sclerosis: an overview", *Neuroimmunol.*, 72:155-161 (1997).

Friedman et al.,"Correction of Aberrant Splicing of the Cystic Fibrosis Transmembrane Conductance Regulator (CFTR) Gene by Antisense Oligonucletide", *J. Biol. Chem.*, 274:36193-36199 (1999).

Greenwald et al., "In Vitro Sensitivity of the Three Mammalian Collagenases to Tetracycline Inhibition: Relationship to Bone and Cartilage Degradation", *Bone*, 22(1):33-38 (1998).

Karras et al., "Deletion of individual Exons and Induction of Soluble Murine Interleukin-5 Receptor-α Chain Expression through Antisense Oligonucleotide-Mediated Redirection of Pre-mRNA Splicing", *Mol. Pharmacol.*, 58:380-387 (2000).

Krawczak et al., "The mutational spectrum of single base-pair substitutions in mRNA splice junctions of human genes: causes and consequences", *Hum. Genet.*, 90:41-54 (1992).

Li et al., "Imunological Characterization of Cell-Surface and Soluble forms of membrane Type 1 Matrix Metalloproteinase in Human Breast Cancer Cells and in Fibroblasts", *Mol. Carcinog.*, 22:84-89 (1998).

Liedtke et al., "Effective Treatment of Models of Multiple Sclerosis by Matrix Metalloproteinase Inhibitors", *Ann. Neurol.*, 44:35-46 (1998).

Nakai et al., "Construction of a novel database containing aberrant splicing mutations of mammalian genes", *Gene*, 14:171-177 (1994).

Philips et al., "Review: RNA processing and human disease", *Cell. Mol. Life Sci.*, 57:235-249 (2000).

Ryan et al., "Potential of tetracyclines to modify cartilage breakdown in osteoarthritis", *Curr. Op. Rheumatol.*, 8:238-247 (1996).

Stetler-Stevenson et al., "Tumor cell interactions with the extracellular matrix during invasion and metastasis", *Annu. Rev. Cell Biol.*, 9:541-573 (1993).

Stoss et al., "Misregulation of pre-mRNA splicing that causes human diseases. Concepts and therapeutic strategies", *Gene Ther, Mol. Biol.*, 5:9-30 (2000).

Tryggvason et al., "Proteolytic degradation of extracellular matrix in tumor invasion", *Biochem. Biophys. Acta*, 907:191-217 (1987).

Van den Bogert et al., "Doxycycline in Combination Chemotherapy of a Rat Leukemia", *Cancer Res.*, 48:6686-6690 (1988).

Wilton et al., "Specific removal of the nonsense mutation from the *mdx* dystrophin mRNA using antisense oligonucleotides", *Neuromuscul. Discord.*, 9:330-338 (1999).

\* cited by examiner

AROMATIC A-RING DERIVATIVES OF TETRACYCLINE COMPOUNDS

RELATED APPLICATIONS

This application claims priority to 60/622,720, filed Oct. 27, 2004, U.S. Provisional Patent Application Ser. No. 60/558,907, filed on Apr. 1, 2004, and U.S. Provisional Patent Application Ser. No. 60/537,228, filed on Jan. 15, 2004. The entire contents of each of which are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention pertains, at least in part, to tetracycline compounds of the formula (I):

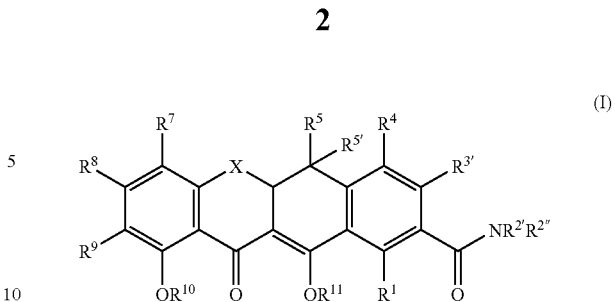

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^{3'}$ is hydroxyl, alkoxy, arylalkyloxy, hydrogen, or a prodrug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$.

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In another embodiment, the invention pertains, at least in part, to 1-dehydrotetracycline compounds. In a further embodiment, the invention pertains to tetracycline compounds of formula (II):

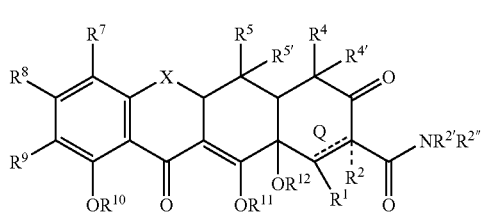

(II)

wherein

R' is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

Q is a double bond when $R^2$ is absent, Q is a single bond when $R^2$ is hydrogen, alkyl, halogen, hydroxyl, thiol, alkenyl, alkynyl, aryl, acyl, formyl, alkoxy, amino, alkylamino, or heterocyclic;

W is $CR^{7d}R^{7e}$, S, NR or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters, prodrugs, and enantiomers thereof.

In another embodiment, the invention pertains, at least in part, to tetracycline compounds of the formula (III):

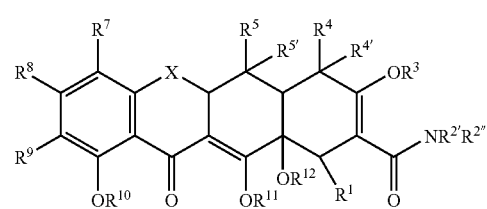

(III)

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each independently hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In yet another embodiment, the invention pertains, at least in part, to tetracycline compound of formula (IV):

(IV)

wherein
$R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

The invention also includes, for example, method for treating a tetracycline responsive state in a subject. The methods include administering to a subject an effective amount of a tetracycline compound of the invention (e.g., a compound of any one of formula I, II, III, IV, or otherwise described herein).

The invention also pertains, at least in part, to pharmaceutical compositions which comprise an effective amount of a tetracycline compound of the invention (e.g., a tetracycline compound of formula I, II, III, IV, or otherwise described herein) and a pharmaceutically acceptable carrier.

The invention also pertains, at least in part, to a method for synthesizing dehydrotetracycline compounds. The method includes contacting a tetracycline compound with an effective amount of a reducing agent to form a 1-hydroxy tetracycline compound; and contacting the 1-hydroxy tetracycline compound with a dehydration agent, to form a dehydrotetracycline compound.

The invention also pertains, at least in part, to a method for synthesizing C1-C2 cleaved tetracycline compounds, by contacting a dehydrotetracycline compound with a cleavage reagent, such that a C1-C2 cleaved tetracycline compound is formed.

In another embodiment, the invention pertains to a method of synthesizing a substituted tetracycline compound, by contacting a dehydrotetracycline compound with a reactive agent, such that a substituted tetracycline compound is formed.

DETAILED DESCRIPTION OF THE INVENTION

1. Aromatized A-Ring and Dehydro Tetracycline Compounds

The invention pertains, at least in part, to novel aromatized A-ring tetracycline derivatives, 1-position derivatives of tetracyclines and 1,2-dehydrotetracycline compounds. It also pertains to tetracycline compounds with a α, β-unsaturated carbonyl functional group at the one position of the tetracycline ring structure.

The term "tetracycline compound" includes many compounds with a similar ring structure to tetracycline. Examples of tetracycline compounds include: tetracycline, oxytetracycline, chlortetracycline, demeclocycline, doxycycline, chelocardin, minocycline, rolitetracycline, lymecycline, sancycline, methacycline, apicycline, clomocycline, guamecycline, meglucycline, mepylcycline, penimepicycline, pipacycline, etamocycline, and penimocycline. Other derivatives and analogues comprising a similar four ring structure are also included. The term includes 4-dedimethylamino derivatives. Table 1 depicts tetracycline and several known tetracycline derivatives. The tetracycline compounds may be unsubstituted at any position or further substituted, for example, at the 2, 4, 5, 6, 7, 8, 9, or 13 position of the ring. The C1 position on each of the tetracycline compounds shown in Table 1 is indicated by an arrow. The A ring is indicated by an "A."

TABLE I

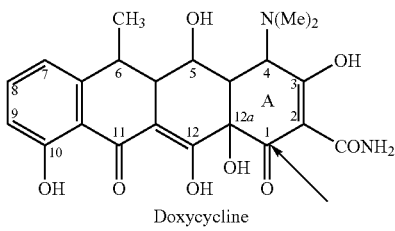

TABLE I-continued

Doxycycline

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a,11a dehydro tetracyclines; 11a C1-6,12 hemiketal tetracyclines; 11a C1-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines. Other examples of tetracycline compounds which may be used to form dehydrotetracycline compounds of the invention include those described in U.S. Published Application 20040002481, incorporated herein by reference.

The term "dehydrotetracycline compounds" includes tetracycline compounds which contain a substituent other than a carboxyl at the C1 position. In an embodiment, the dehydrotetracycline compound is dehydrotetracycline (e.g., wherein $R^4$ is $NR^{4a}R^{4b}$; $R^{4'}$ and $R^{4b}$ are methyl, $R^{4'}$, $R^5$, and $R^{5'}$ are hydrogen and X is $CR^6R^{6'}$ wherein $R^6$ is methyl and $R^{6'}$ is hydroxy); dehydrodoxycycline (e.g., wherein $R^4$ is $NR^{4a}R^{4b}$; $R^{4a}$ and $R^{4b}$ are methyl, $R^5$ is hydroxyl, $R^{4'}$ and $R^{5'}$ are hydrogen, and X is $CR^6R^{6'}$, wherein $R^6$ is methyl and $R^{6'}$ is hydrogen); dehydrominocycline (wherein $R^4$ is $NR^{4a}R^{4b}$; $R^{4a}$ and $R^{4b}$ are methyl; $R^{4'}$, $R^{5'}$, and $R^5$ are hydrogen and X is $CR^6R^{6'}$ wherein $R^6$ and $R^{6'}$ are hydrogen atoms, and $R^7$ is dimethylamino); or dehydrosancycline (wherein $R^4$ is $NR^{4a}R^{4b}$; $R^{4a}$ and $R^{4b}$ are methyl; $R^{4'}$, $R^{5'}$, and $R^5$ are hydrogen and X is $CR^6R^{6'}$ wherein $R^6$ and $R^{6'}$ are hydrogen atoms. In one embodiment, $R^4$ and $R^{4'}$ are each hydrogen or the oxygen of a carbonyl group. In a further embodiment, the dehydrotetracycline compound is a 1,2-dehydrotetracycline compound. In another further embodiment, the dehydrotetracycline compound contains an α,β-unsaturated carbonyl functional group, wherein the unsaturation is between C1 and C2 of the tetracycline ring structure.

In one embodiment, the invention pertains, at least in part, to tetracycline compounds of the formula (I):

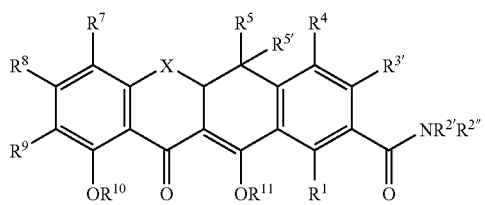

(I)

wherein
- $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;
- $R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{10}$, $R^{11}$ and $R^{12}$ are each independently hydrogen, alkyl, aryl, benzyl, arylalkyl, or a pro-drug moiety;
- $R^{3'}$ is hydroxyl, alkoxy, arylalkyloxy, hydrogen, or a prodrug moiety;
- $R^4$ is $NR^{4a}R^{4b}$, alkyl, alkenyl, alkynyl, hydroxyl, halogen, or hydrogen;
- $R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
- $R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
- $R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{7c}C(=W')WR^{7a}$;
- $R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{8c}C(=E')ER^{8a}$;
- $R^9$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{9c}C(=Z')ZR^{9a}$;
- $R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$,
- $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{13}$ is hydrogen, hydroxy, alkyl, alkenyl, alkynyl, alkoxy, alkylthio, aryl, alkylsulfinyl, alkylsulfonyl, alkylamino, or an arylalkyl;
- E is $CR^{8d}R^{8e}$, S, $NR^{8b}$ or O;
- E' is O, $NR^{8f}$, or S;
- W is $CR^{7d}R^{7e}$, S, $NR^{7b}$ or O;
- W' is O, $NR^{7f}$, or S;
- X is $CHC(R^{13}Y'Y)$, $C=CR^{13}Y$, $CR^6R^{6'}$, S, $NR^6$, or O;
- Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;
- Z is $CR^{9d}R^{9e}$, S, $NR^{9b}$ or O;
- Z' is O, S, or $NR^{9f}$, and pharmaceutically acceptable salts, esters and enantiomers thereof.

In one embodiment, the compound of the invention is

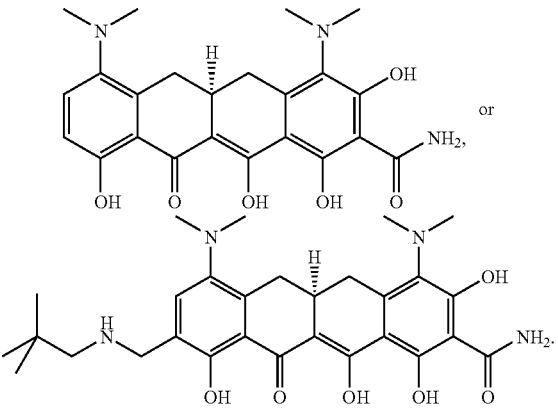

In one embodiment, the invention pertains, at least in part, to tetracycline compounds of the formula (II):

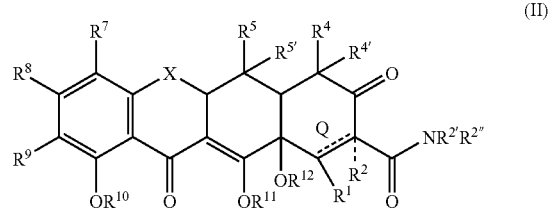

(II)

wherein
- $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;
- $R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;
- $R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

Q is a double bond when $R^2$ is absent, Q is a single bond when $R^2$ is hydrogen, alkyl, halogen, hydroxyl, thiol, alkenyl, alkynyl, aryl, acyl, formyl, alkoxy, amino, alkylamino, cyano, nitro, or heterocyclic;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^6R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In a further embodiment, $R^9$ is not —$CH_2NHCH_2(CH_3)_3$ when $R^7$ is H, X is $CHCH_3$, $R^5$ is OH, $R^1$ is H and Q is a double bond. In one embodiment, the tetracycline compound is a 1,2-dehydrodoxycycline compound of the formula:

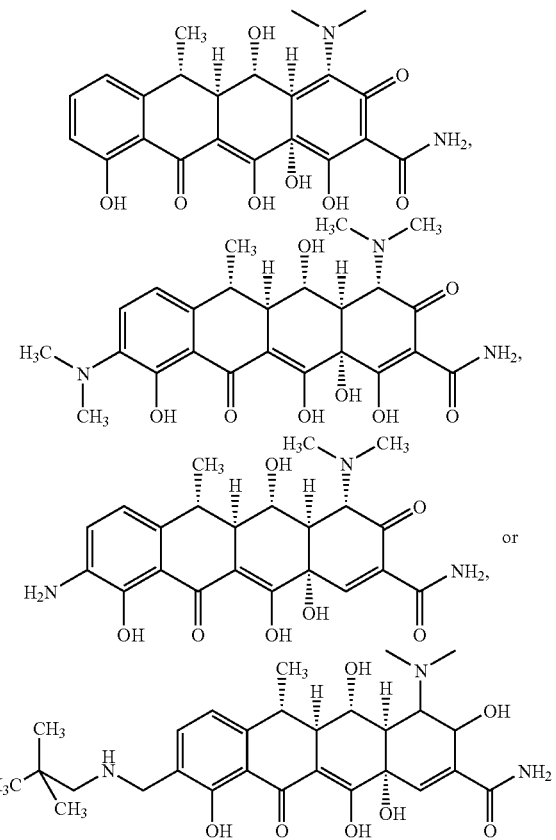

In another embodiment, the invention pertains, at least in part, to tetracycline compounds of the formula (III):

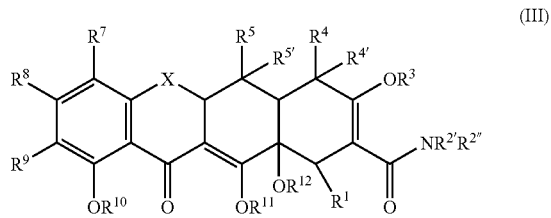

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^3$, $R^{10}$, $R^{11}$ and $R^{12}$ are each independently hydrogen, alkyl, aryl, benzyl, arylalkyl, or a pro-drug moiety;

$R^4$ and $R^{4'}$ are each independently $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{7c}CC(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{8c}(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In another embodiment, the invention pertains to tetracycline compounds of formula (IV):

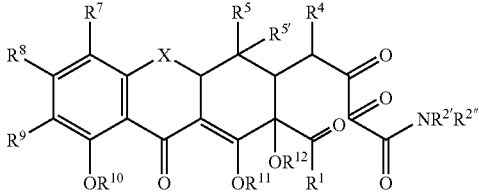

(IV)

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen;

$R^{2'}$, $R^{2''}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$ and $R^{12}$ are each independently hydrogen, alkyl, aryl, benzyl, arylalkyl, or a pro-drug moiety;

$R^4$ is $NR^{4a}R^{4b}$, alkyl, alkenyl, alkynyl, hydroxyl, halogen, or hydrogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}NR^{8c}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$, or S;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In another embodiment, the tetracycline compound of formula I, II, III, or IV, is a dehydro sancycline compound, wherein $R^{2'}$, $R^3$, $R^{10}$, $R^{11}$, and $R^{12}$ are each hydrogen or a prodrug moiety; $R^4$ is $NR^{4a}R^{4b}$; $R^a$ and $R^{4b}$ are each alkyl; X is $CR^6R^{6'}$; and $R^{2''}$, $R^{4'}$, $R^5$, $R^{5'}$, $R^6$, and $R^{6'}$ are each hydrogen.

In another embodiment, the tetracycline compound of formula I, II, III, or IV, is a dehydro tetracycline compound, wherein $R^4$ is $NR^{4a}R^{4b}$; $R^{4a}$ and $R^{4b}$ are each alkyl; $R^5$ and $R^{5'}$ are hydrogen and X is $CR^6R^{6'}$, wherein $R^6$ is methyl and $R^{6'}$ is hydroxy.

In another embodiment, the tetracycline compound of formula I, II, III, or IV, is a dehydro doxycycline compound, wherein $R^4$ is $NR^{4a}R^{4b}$; $R^{4a}$ and $R^{4b}$ are each alkyl (e.g., methyl); $R^5$ is hydroxyl; X is $CR^6R^{6'}$; $R^6$ is methyl; and $R^{5'}$ and $R^{6'}$ are hydrogen.

In another embodiment, the tetracycline compound of formula I, II, III, or IV, is a dehydro minocycline compound, wherein $R^4$ is $NR^{4a}R^{4b}$; $R^{4a}$ and $R^{4b}$ are each alkyl (e.g., methyl); X is $CR^6R^{6'}$; $R^5$, $R^{5'}$, $R^6$ and $R^{6'}$ are hydrogen atoms and $R^7$ is dimethylamino.

In an embodiment, the invention pertains to tetracycline compounds of formula I, II, III, and IV, wherein $R^1$ is hydrogen, halogen (e.g., fluorine, chlorine, bromine, iodine, etc.), hydroxy, thiol, amino, cyano, acyl, alkoxy, carboxyl, amido, alkyl, alkenyl, alkynyl, aryl, heterocyclic, alkylamino, or any other substituent which allows the tetracycline compound to perform its intended function.

In another embodiment, the invention pertains to tetracycline compounds of formula II, wherein Q is a single bond. When Q is a single bond, the invention pertains to tetracycline compounds wherein $R^2$ is hydrogen, halogen, cyano, alkyl, hydroxy, alkoxy, or any other substituent which allows the compounds of the invention to perform their intended function. In another embodiment, the invention pertains to tetracycline compounds of formula I, wherein Q is a double bond. In another embodiment, the invention pertains to tetracycline compounds wherein $R^1$ and $R^2$ are linked to form a ring. In one embodiment, $R^1$ and $R^2$ are linked to form an epoxide, a lactam, a lactone, a carboxylic ring, a heterocyclic ring, or other ring structure. In one embodiment, $R^1$ and $R^2$ are linked to form a 3, 4, 5, 6, 7, 8, or 9 membered ring.

In a further embodiment, $R^9$ is hydrogen. In another embodiment, $R^9$ is substituted or unsubstituted aryl (e.g., substituted or unsubstituted carbocyclic, e.g., phenyl or naphthyl; or substituted or unsubstituted heteroaryl). $R^9$ also may be substituted or unsubstituted alkenyl or substituted or unsubstituted alkynyl. $R^9$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety.

In another further embodiment, $R^9$ is substituted or unsubstituted alkyl. In a further embodiment, $R^9$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl.

In another embodiment, $R^9$ is substituted or unsubstituted amino, e.g., alkylamino, dialkylamino, arylamino, alkyl carbonylamino, alkyl aminocarbonylamino, arylcarbonylamino, etc. In another embodiment, $R^9$ is amido. In yet another embodiment, $R^9$ is cyano, halogen (e.g., fluorine, bromine, chlorine, iodo, etc.), nitro, hydroxyl, alkoxy, or any other substituent which allows the tetracycline compound to perform its intended function. In another embodiment, $R^9$ is an $R^9$ moiety described in WO 03/079984; WO 03/075857; WO 02/04406; or WO 01/74761, incorporated herein by reference in its entirety.

In a further embodiment, $R^7$ is hydrogen. In another embodiment, $R^7$ is substituted or unsubstituted aryl (e.g., substituted or unsubstituted carbocyclic, e.g., phenyl or naphthyl; or substituted or unsubstituted heteroaryl). $R^7$ also may be substituted or unsubstituted alkenyl or substituted or unsubstituted alkynyl. $R^7$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety.

In another further embodiment, $R^7$ is substituted or unsubstituted alkyl. In a further embodiment, $R^7$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl.

In another embodiment, $R^7$ is substituted or unsubstituted amino, e.g., alkylamino, dialkylamino, arylamino, alkyl carbonylamino, alkyl aminocarbonylamino, arylcarbonylamino, etc. In another embodiment, $R^7$ is amido. In yet another embodiment, $R^7$ is cyano, halogen (e.g., fluorine, bromine, chlorine, iodo, etc.), nitro, hydroxyl, alkoxy, or any other substituent which allows the tetracycline compound to perform its intended function. In another embodiment, $R^7$ is a 7-position moiety described in WO 02/04407, WO 01/74761, WO 03/079984, or WO 03/075857, incorporated herein by reference in their entirety.

In a further embodiment, $R^8$ is hydrogen. In another embodiment, $R^8$ is substituted or unsubstituted aryl (e.g., substituted or unsubstituted carbocyclic, e.g., phenyl or naphthyl; or substituted or unsubstituted heteroaryl). $R^8$ also may be substituted or unsubstituted alkenyl or substituted or unsubstituted alkynyl. $R^8$ also may be heterocyclic or alkylcarbonyl, alkenylcarbonyl, alkynylcarbonyl, alkyloxycarbonyl, or otherwise comprise a substituted carbonyl, acyl, acetyl, or formyl moiety.

In another further embodiment, $R^8$ is substituted or unsubstituted alkyl. In a further embodiment, $R^8$ is aminoalkyl, e.g., aminomethyl. In a further embodiment, the aminoalkyl is further substituted with any substituent which allows the compound to perform its intended function. In a further embodiment, the aminoalkyl substituent is alkylaminomethyl.

In another embodiment, $R^8$ is substituted or unsubstituted amino, e.g., alkylamino, dialkylamino, arylamino, alkyl carbonylamino, alkyl aminocarbonylamino, arylcarbonylamino, etc. In another embodiment, $R^8$ is amido. In yet another embodiment, $R^8$ is cyano, halogen (e.g., fluorine, bromine, chlorine, iodo, etc.), nitro, hydroxyl, alkoxy, or any other substituent which allows the tetracycline compound to perform its intended function. In another embodiment, $R^8$ is an $R^8$ moiety described in WO 02/12170, WO 02/04404, or WO 03/079984, incorporated herein by reference in their entirety.

In another embodiment, $R^3$, $R^{10}$, $R^{11}$, and $R^{12}$ are each independently hydrogen, alkyl, acyl, aryl, or arylalkyl. Other $R^3$, $R^{10}$, $R^{11}$, and $R^{12}$ moieties are described in U.S. Ser. No. 10/619,653, incorporated herein by reference in its entirety. Other examples of $R^{2'}$ and $R^{2''}$ moieties are described in U.S. Published Application 20040002481.

Examples of dehydrotetracycline compounds of the invention include the following compounds:

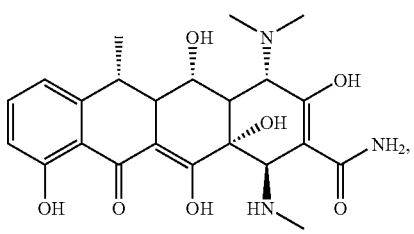

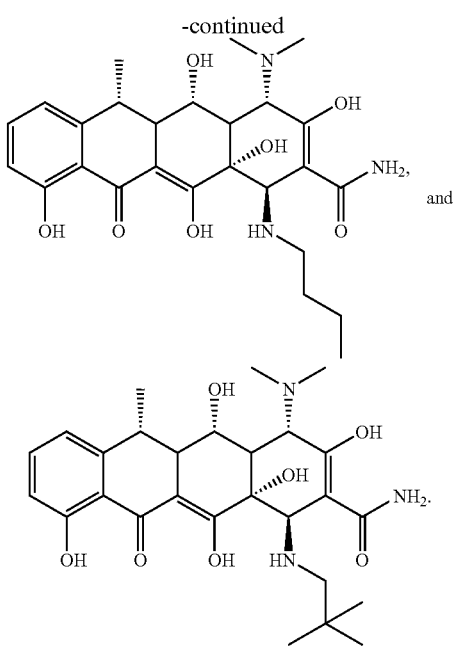

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxophenyl, quinoline, isoquinoline, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

2. Methods for Synthesizing Dehydrotetracycline Compounds

A method for derivatizing tetracycline compounds at the 1 position has been discovered through chemical modification via reduction of C1 carbonyl to produce a C1 hydroxyl group. The hydroxyl group is dehydrated to produce C1-C2 dehydrotetracyclines with a reactive α,β-unsaturated carbonyl functional group, as shown in Scheme 1:

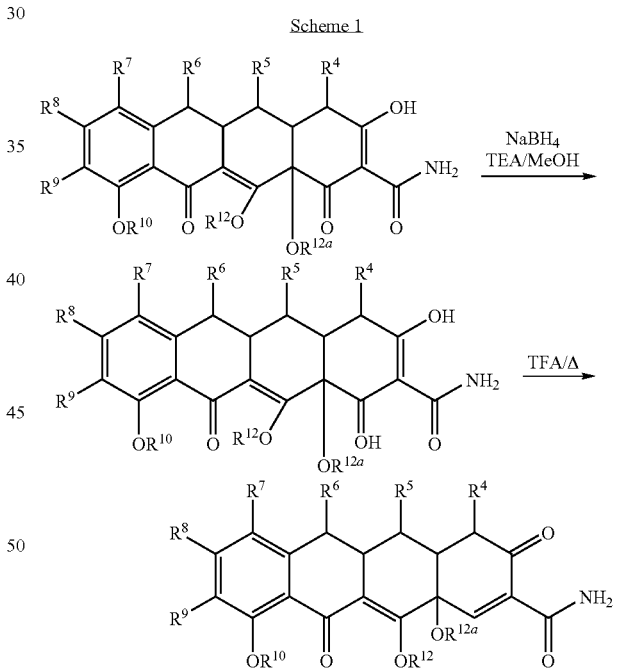

In one embodiment, the invention pertains to a method for synthesizing dehydrotetracycline compounds. The method includes contacting a tetracycline compound with an effective amount of a reducing agent to form a 1-hydroxy tetracycline compound, and contacting the 1-hydroxy tetracycline compound with a dehydration agent, such that a dehydrotetracycline compound is formed. In a further embodiment, the dehydrotetracycline compound that is formed comprises an α,β-unsaturated carbonyl functional group.

The term "reducing agent" includes agents which are capable of reducing the C1 carbonyl to a hydroxyl group.

Examples of reducing agents are described in Comprehensive Organic Transformations ("COT") $2^{nd}$ Ed., Larock, 304, 305. In one embodiment, the reducing agent is sodium borohydride.

The term "1-hydroxy tetracycline compounds" include compound which have a hydroxyl group at the C1 position, e.g., compounds of Formula II, wherein $R^1$ is hydroxy.

Dehydration agents are also known in the art. Examples of dehydration agents are described in Comprehensive Organic Transformations ("COT") $2^{nd}$ Ed., Larock, 304, 305, incorporated herein by reference. In one embodiment, the dehydration agent is an acid, e.g., trifluoroacetic acid and/or heat.

functional group, e.g., at the C1-C2 position. In Scheme 2, the α,β-unsaturated carbonyl functional group at the C1-C2 position is indicated by the box.

A wide range of tetracycline compounds of the invention can be synthesized using the methods of the invention. The tetracycline compounds of the invention can be synthesized, for example, by reacting various reactive agent, such as nucleophiles, with the dehydrotetracycline to produce tetracycline compounds of the invention. Examples of some of the substituted tetracyclines which can be synthesized using the methods of the invention include compounds with C1-carbon-carbon, C1-carbon-nitrogen and C1-carbon-oxygen or C1-carbon-heteroatom bonds at the $R^1$ position, as shown in Scheme 2.

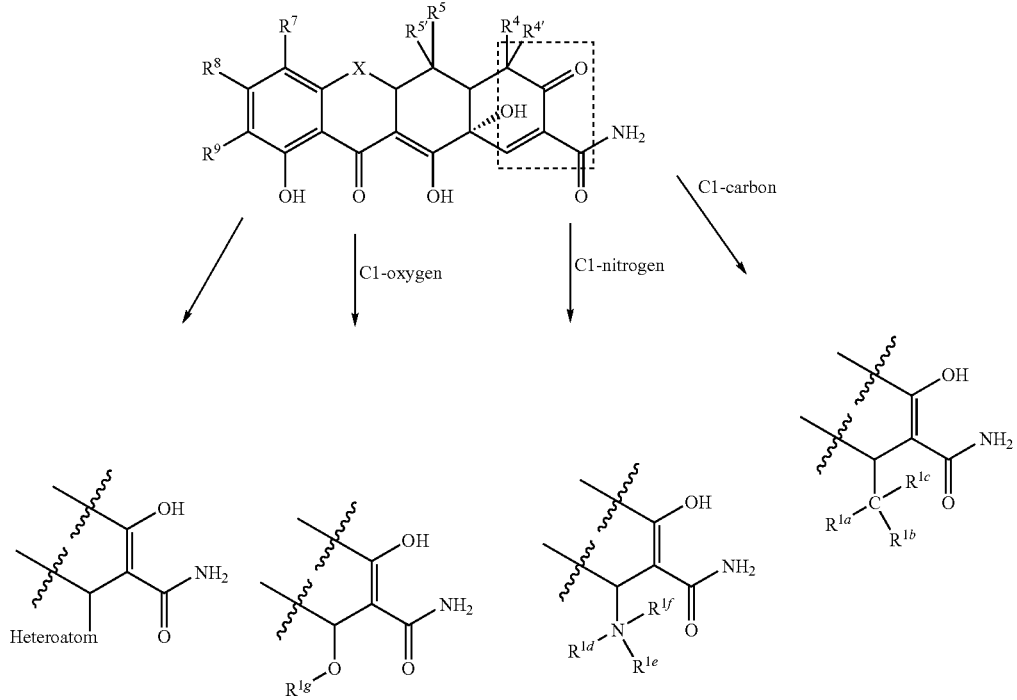

Scheme 2

In one embodiment, the tetracycline compound is tetracycline, doxycycline, methacycline, minocycline, or sancycline. In another embodiment, the tetracycline compound is a tetracycline compound described in, for example, WO 03/079983, WO 02/12170, WO 02/04407, WO 02.04406, WO 02/04405, WO 02/04404, WO 01/74761, WO 03/079984, WO 03/075857, WO 03/057169, WO 02/072545, WO 02/072506, U.S. Ser. Nos. 10/619,653, 09/895,857; 09/895,812; U.S. Pat. Nos. 5,326,759; 5,328,902; 5,495,031; 5,495,018; 5,495,030; 5,495,032; 5,512,553; 5,675,030; 5,843,925; 5,886,175; 6,165,999; 3,239,499; WO 95/22529; U.S. Pat. Nos. 5,064,821; 5,589,470; 5,811,412, or U.S. Application 20040002481.

In another embodiment, the invention pertains to a method for synthesizing a substituted tetracycline compound. The method includes contacting a dehydrotetracycline compound with a reactive agent, such that a substituted tetracycline compound is formed. In one embodiment, the dehydrotetracycline compound comprises an α,β-unsaturated carbonyl In Scheme 2, $R^{1a}$, $R^{1b}$, $R^{1c}$, $R^{1d}$, $R^{1e}$, $R^{1f}$, and $R^{1g}$ are each independently hydrogen, alkyl, heterocyclic, aryl, alkenyl, alkynyl, alkoxy, carbonyl, acyl, halogen, cyano, amino, amido, nitro, or any other substituent described herein which would allow the tetracycline compounds of the invention to perform their intended functions.

Tetracycline compounds of the invention can be synthesized using methods and reactive agents known the art to react with α,β-unsaturated ketones. For example, anions, carbanions and alkali metals are reactive agents which react to give tetracycline compounds of the invention with various $R^1$ substituents (Scheme 3). Other reactive agents which can be used to synthesize the compounds of the invention with various $R^1$ substituents include alkali metal acetylides, lithium dialkyl cuprates, lithium diarylcuprates with or without complexing ligands. Tetracycline compounds with $R^1$ substituents can also be formed using reactive agents such as anions, e.g., anions generated from ketones, aldehydes and the like. Reactive agents also include organometallic reagents such as Grignards and organolithium and ylide reagents (COT, 351-401, Scheme 3).

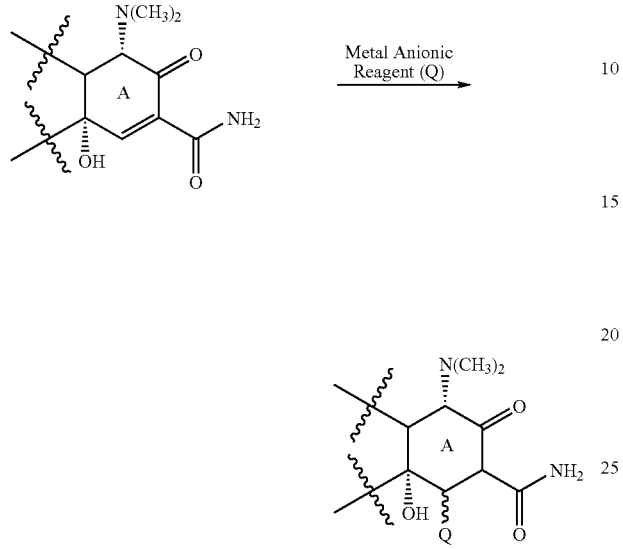

Scheme 3

Other reactive agents which can be used include those used in enol-ester (COT, 1485-1487) and enol silane (COT, 1488-1505) reactions. Other reactive agents include hydration agents. Hydration can be used to introduce $R^1$ hydroxyl groups (COT, 991-995). Tetracycline compounds of the invention wherein $R^1$ is hydroxyl can be formed also by hydroboration followed by oxidation to an alcohol (COT, 1005-1008). The tetracycline compounds having a substituted carbonyl at the $R^1$ position can be synthesized by carbonylation (COT, 1009-1011, 1690-1693).

Tetracycline compounds of the invention having alkyl and other substituents at the $R^1$ position can be synthesized sing a variety of reactive agents via free radical, Michael and Michael-like addition reactions, and organoboron reactions. Other possible reactive agents include catalysts which can be used to synthesize various tetracycline compounds of the invention include aluminum, gallium, thallium, silicon, germanium, tin, lead, stilbine, titanium, zirconium, manganese, iron, cobalt, rhodium, nickel, palladium, copper, silver, zinc, mercury, and others (COT, 1560-1616). Tetracycline compounds of the invention wherein $R^1$ is cyano can also be formed using reactive agents (COT, 1705-1706). Tetracycline compounds of the invention wherein $R^1$ is an ester can be synthesized, for example, using ester additions (COT, 1724-1725). Tetracycline compounds of the invention wherein $R^1$ comprises a nitrile group can be synthesized using nitrile addition reagents (COT, 1800-1801) as the reactive agent. Tetracycline compounds wherein $R^1$ is a formyl or other carbonyl group can be synthesized using hydroformylation reagents (COT, 1363-1380) as the reactive agent.

Tetracycline compounds of the invention wherein $R^1$ is an amide can be synthesized via amide conjugations (COT, 1701).

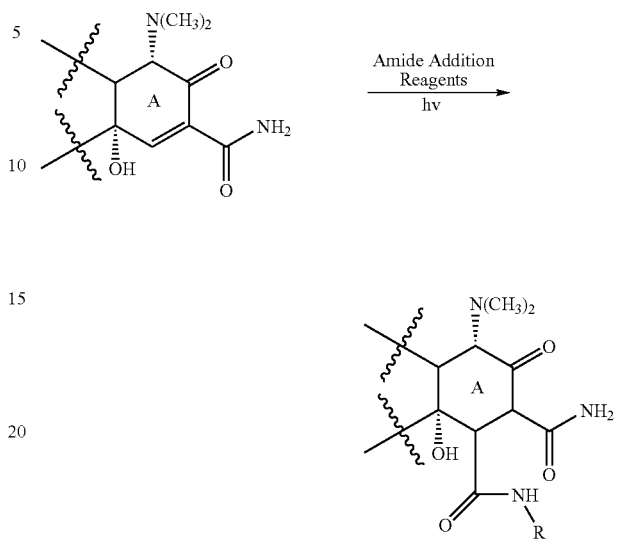

Scheme 4

Tetracycline compounds of the invention include compounds wherein $R^1$ is an primary, secondary, or tertiary amine. Examples of reactive agents include primary and secondary amines. Amines can be formed using techniques known in the art (COT, 761-778). Tetracycline compounds of the invention with an amino $R^1$ substituent may also be used to form prodrugs based upon their reactivity with prodrug-forming reactive agents.

Tetracycline compounds of formula I, wherein Q is a double bond and $R^1$ is alkyl, alkenyl, alkynyl, or aryl can be synthesized using, for example, conjugate addition reactive agents as shown in Scheme 5 (COT, 1806-1841).

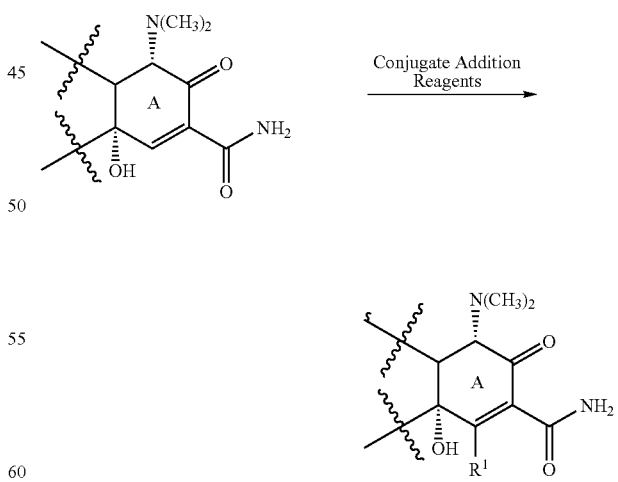

Scheme 5

Tetracycline compounds of the invention wherein $R^2$ is alkyl, alkenyl, alkynyl, aryl, etc. can be synthesized, for example, using a variety of reactive agents such as metal anionic reagents (Scheme 6) and by the alkylation of enones (COT, 1546-1557).

Scheme 6

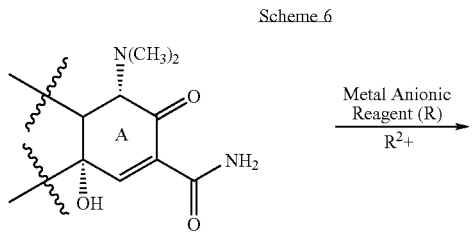

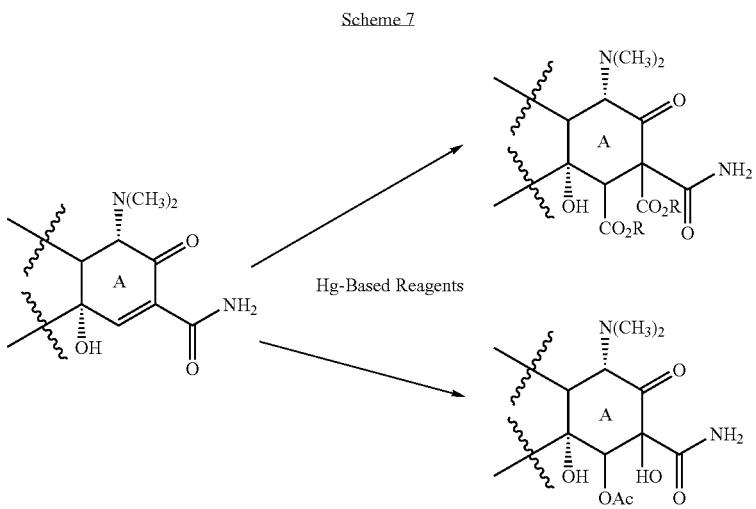

-continued

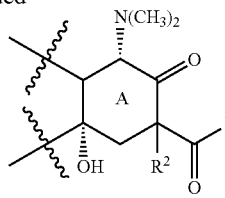

Tetracycline compounds wherein $R^2$ is hydroxy or a carbonyl group may be synthesized using asymmetric hydroboration (COT, 1008).

Tetracycline compounds of the invention may also be formed using reactions such as reductions via catalytic hydrogenation, selective hydrogenation, enantioselective hydrogenation, hydroboration-protonolysis, conjugate reduction, reduction dimerization (COT $2^{nd}$ Ed., Larock, pg 7-29), and coupling reactions (COT, 81).

Other tetracycline compounds of the invention wherein Q is a single bond, can be synthesized using a variety of reactive agents such as organosilicon reagents (COT, 108), organozirconium reagents (COT, 114), organonickel reagents (COT, 116-117), and organomercury (COT, 124) reagents.

Tetracycline compounds of the invention wherein $R^1$ and $R^2$ are halogens can be formed by, for example, halogen addition reactions (COT, 629-647). Tetracycline compounds of the invention wherein $R^1$ is alkyl and $R^2$ is halogen can be formed, for example, by haloalkylation reactions (COT, 647-653). Tetracycline compounds of the invention wherein $R^1$ and $R^2$ are hydroxyl can be synthesized by, for example, cis-hydroxylation (COT, 996-1001) and transhydroxylation (COT, 1001-1003).

Tetracycline compounds of the invention wherein $R^1$ and $R^2$ are carboxylate, alkyloxycarbonyl, aryloxycarbonyl, acetyl, hydroxyl, etc. can be synthesized using, for example, solvomercuration and demercuration (COT, 1629-1632) reactions (Scheme 7).

Scheme 7

The invention also pertains to tetracycline compounds with an aromatized A ring. The aromatized A ring tetracycline compounds can be formed by aromatization reactions known in the art (COT 653).

In a further embodiment, the invention pertains to methods for synthesizing C1-C2 cleaved tetracycline compounds, by contacting a dehydrotetracycline compound with a cleavage reagent, such that C1-C2 cleaved tetracycline compounds are formed. Examples of C1-C2 cleaved tetracycline compounds include compounds of formula IV. Cleavage and ozonolysis reagents are described in COT 1210-1215, 1630-1634.

Tetracycline compounds of the invention wherein $R^1$ and $R^2$ are linked to form a ring can be synthesized by reacting the alkene to form a heterocycle such as a lactone or lactam (COT, 1876-1904), as shown in Scheme 8. Tetracycline compounds of the invention wherein $R^1$ and $R^2$ are linked to form an epoxide are also included (COT, 915-927).

Scheme 8

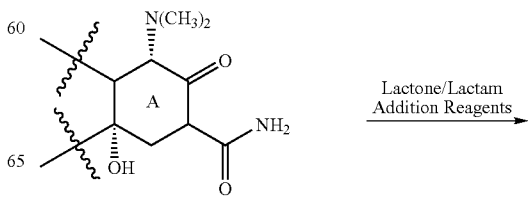

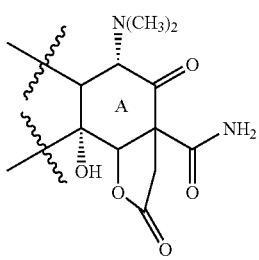

Tetracycline compounds of the invention also include compounds wherein $R^1$ and $R^2$ are linked to form rings with 3 (COT, 135) or more (COT, 136-186) members. Tetracycline compounds of the invention wherein $R^1$ and $R^2$ are linked to form a ring can also be synthesized via Diels-Alder reactions (COT 537), as well as other cyclization, reactions with ketenes (COT, 1340-1345), annulations (COT, 1345-1362) and related reactions (COT, 537-560). Other ring forming reactions which can be used to synthesize compounds of the invention include alkene additions using hv or boron reagents forming oxetanes and higher member rings (COT, 913-914, Scheme 6).

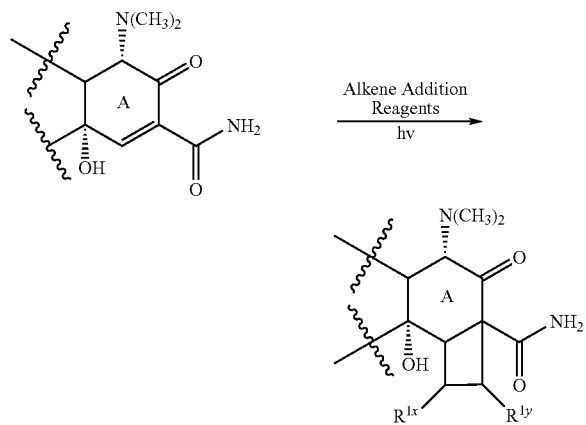

The tetracycline compounds of the invention also include tetracycline compounds with substituents at the 3, 4, 5, 6, 7, 8, 9, 10, 11, 12, etc. positions. For example in Scheme 10, a 1,2-dehydro doxycycline is substituted at the $R^9$ position by an amino functional group. This compound retains activity in inflammation models. Scheme 10 shows the derivatization of a 1,2-dehydrotetracycline compound at the 9 position.

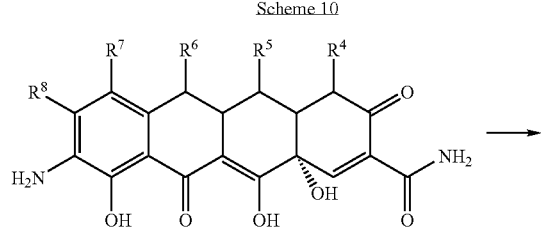

Examples of reactions which can be used to synthesize the dehydrotetracycline compounds of the invention include those described in, for example, WO 03/079983, WO 02/12170, WO 02/04407, WO 02.04406, WO 02/04405, WO 02/04404, WO 01/74761, WO 03/079984, WO 03/075857, WO 03/057169, WO 02/072545, WO 02/072506, U.S. Ser. Nos. 10/619,653, 09/895,857; 09/895,812; U.S. Pat. Nos. 5,326,759; 5,328,902; 5,495,031; 5,495,018; 5,495,030; 5,495,032; 5,512,553; 5,675,030; 5,843,925; 5,886,175; 6,165,999; 3,239,499; WO 95/22529; U.S. Pat. Nos. 5,064,821; 5,589,470; and 5,811,412, all incorporated herein by reference. In an embodiment, the present invention also pertains to 1,2-dehydro and aromatzed A-ring derivatives of each of the tetracycline compounds disclosed in each of the above references.

In another embodiment, the invention pertains to tetracycline compounds synthesized by the methods described herein.

3. Methods for Using Aromatized A-ring and Dehydro Tetracycline Compounds

The invention also pertains to methods for treating a tetracycline responsive states in subjects, by administering to a subject an effective amount of a tetracycline compound of the invention (e.g., a compound of Formula I, II, III, IV, or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention, e.g., a tetracycline compound of formula I, II, III, IV, or otherwise described herein). Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 µg/ml (as measured by assays known in the art and/or the assay given in Example 2).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention, e.g., a compound of formula I, II, III, IV, or otherwise described herein. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention, e.g., a tetracycline compound of formula I, II, III, IV, or otherwise described herein.

Examples of matrix metalloproteinase associated states ("MMPAS's") include, but are not limited to, arteriosclerosis, corneal ulceration, emphysema, osteoarthritis, multiple sclerosis (Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontis, osteoporosis, rheumatoid arthritis, ulcerative colitis, inflammatory disorders, tumor growth and invasion (Stetler-Stevenson et al., *Annu. Rev. Cell Biol.* 1993, 9:541-73: Tryggvason et al., *Biochim. Biophys. Acta* 1987, 907:191-217; Li et al., *Mol. Carcinog.* 1998, 22:84-89)), metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8;238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis (e.g., including but not limited to, relapsing and remitting multiple sclerosis, primary progressive multiple sclerosis, and secondary progressive multiple sclerosis), amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent who is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. No. 6,100,248; 5,843,925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; U.S. Pat. Nos. 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphysema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. No. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards, Document M7-A2*, vol. 10, no. 8, pp. 13-20, 2$^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier. The tetracycline compounds of the invention may also be used to treat fungal disorders, viral disorders, parasitic disorders, and other disorders described in WO 03/005971, WO 02/085303, WO 02/072022, WO 02/072031, WO 01/52858, and U.S. Ser. No. 10/692,764, each of which is incorporated herein by reference in its entirety.

In another embodiment, the tetracycline responsive state is a disorder treated by modulation of RNA.

The term "disorders treatable by modulation of RNA" or "DTMR" includes viral, neurodegenerative and other disorders which are caused or related to RNA function, structure, amounts and/or other activities of RNA which are lower or higher than desired and those disorders treatable by compounds described herein. Examples of DTMR include viral disorders (e.g., retroviral disorders (e.g., HIV, etc.), disorders caused by human rhinovirus RNA and proteins, VEE virus, Venezuelan equine encephalitis virus, eastern X disease, West Nile virus, bacterial spot of peach, camelpox virus, potato leafroll virus, stubborn disease and infectious variegations of citrus seedlings, viral protein synthesis in *Escherichia coli* infected with coliphage MS2, yellow viruses, citrus greening disease, ratoon stunting disease, European yellows of plants, inclusion conjunctivitis virus, meningopneumonitis virus, trachoma virus, hog plague virus, ornithosis virus, influenza virus, rabies virus, viral abortion in ungulates, pneumonitis, and cancer.

Other exemplary DTMRs include disorders caused by, or associated with splicing. For example, some disorders associated with defects in pre-mRNA processing result from a loss of function due to mutations in regulatory elements of a gene. Examples of such mutations are described in Krawczak et al. (1992) *Hum. Genet,* 90:41-54; and Nakai et al. (1994) *Gene* 14:171-177. Other DTMR include disorders which have been attributed to a change in trans-acting factors. Examples of DTMRs which are associated with splicing include those described in Philips et al. (2000), *Cell. Mol. Life Sci.,* 57:235-249), as well as, FTDP-17 (frontotemporal dementia with parkinsonism) and β-thalassemia.

Certain DTMRs associated with splicing include those which are generated by point mutations that either destroy splice-sites or generate new cryptic sites in the vicinity of normally used exons. Examples of such DTMRs include cystic fibrosis (Friedman et al. (1999) *J. Biol. Chem.* 274:36193-36199), muscular dystrophy (Wilton et al. (1999) *Neuromuscul. Disord.* 9:330-338), and eosinophilic diseases (Karras et al. (2000) *Mol. Pharamcol.* 58:380-387).

Other DTMRs include cancers which may change splicing patterns during cancer formation and progression. Example of such cancers include, but are not limited to leukemia, colon/rectal cancer, myeloid leukemia, breast cancer, gastric carcinomas, acute leukemia, multiple myeloma, myeloid cell leukemia, lung cancer, prostate cancer, etc. Addition DTMRs associated with splicing are discussed in Stoss et al., (2000), *Gene Ther. Mol. Biol.* 5:9-30).

Another example of a DTMR is a cancer in which treatment of the cancer cells with a tetracycline compound results in the modulation of RNA, where the modulation of RNA increases the susceptibility of the cell to a second agent, e.g., a chemotherapeutic agent. Such DTMRs can be treated using a combination of the tetracycline compound and a chemotherapeutic agent. Exemplary cancers include those in which the tetracycline compound modulates the form of BCL expressed by the cells.

Other DTMRs include disorders wherein particular ribozymes are present in aberrant quantities. Examples include breast cancer, hepatitis C virus (HCV), liver cirrhosis, and heptacellular carcinoma.

The language "effective amount" of the compound is that amount necessary or sufficient to treat or prevent a tetracycline compound responsive state. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a tetracycline compound (e.g., a tetracycline compound of the formula I, II, III, IV, or otherwise described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is derivatized with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, or otherwise described herein, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below and/or by using literature techniques known to those of ordinary skill in the art.

EXAMPLE 1

Synthesis of A-Ring Aromatized Minocycline

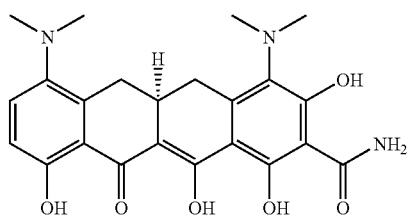

Minocycline 2HCl (0.5 g, 1 mM) was suspended in 25 mL of 1:4 DMF/toluene and 200 µL of acetic anhydride (2 mM) added followed by 10 µL of $H_2SO_4$. The solution was reluxed overnight and the solvent removed in vacuo. The crude solid was dissolved in methanol (25 mL), 1 mL of concentrated HCl and 200 µL of thionyl chloride was added. The solution was stired at room temperature for 4 hours and the solvent removed in vacuo. The residue was dissolved in a minimal amount of MeOH and the compound purified by reversephase C18 preparative chromatography to yield the yellow-green compound as the 2TFA salt LCMS (M+H): 440.

EXAMPLE 2

Synthesis of 9-Amino-1-Dehydrodoxycycline

Triethylamine was added to a solution of doxycycline (1 g, 2.2 mmole) in 15 ml of methanol to bring the pH to about 9. Then, 426 mg of sodium borohydride (5 eq) was added to this mixture portionwise. The resulting reaction mixture was stirred at room temperature for several hours. The reaction was monitored by analytical HPLC and LCMS [MS: 445 (for starting material) and MS 447 (for product)]. The solvent was removed and the residue was diluted with water. The aqueous solution was then extracted with n-butanol (2×). The combined organic fractions were evaporated under reduced pressure to give the C1 alcohol. This material was redissolved in 20 ml of trifluoroacetic acid and heated at 60 for several hours. The reaction was monitored by analytical HPLC and LCMS [MS: 447 for the alcohol and 429 for the dehydrated material). At the completion of the reaction, the TFA was evaporated and the residue was dissolved in a mixture of methanol/water (3:1). The solution was filtered and the desired material isolated via preparative HPLC. About 250 mg of light yellow solid was obtained (MS: 429). The chemical structure was further characterized by NMR.

1 mmol of dehydro-doxycycline trifluoroacetate in 15 ml of DMF was reacted with 4 equivalent of amine and in the presence of 1 equivalent of InCl$_3$. The reaction mixture was stirred at room temperature for several hours. The desired material was isolated via preparative HPLC.

EXAMPLE 3

In Vitro Minimum Inhibitory Concentration (MIC) Assay

The following assay is used to determine the efficacy of tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of 1'10$^6$ CFU/ml. At OD=1, cell densities for different genera should be approximately:

| | |
|---|---|
| E. coli | 1 × 10$^9$ CFU/ml |
| S. aureus | 5 × 10$^8$ CFU/ml |
| Enterococcus sp. | 2.5 × 10$^9$ CFU/ml |

50 μl of the cell suspensions are added to each well of microtiter plates. The final cell density should be approximately 5×10$^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

Compounds which were found to have low antibacterial activity include the compounds of Table 2, below.

TABLE 2

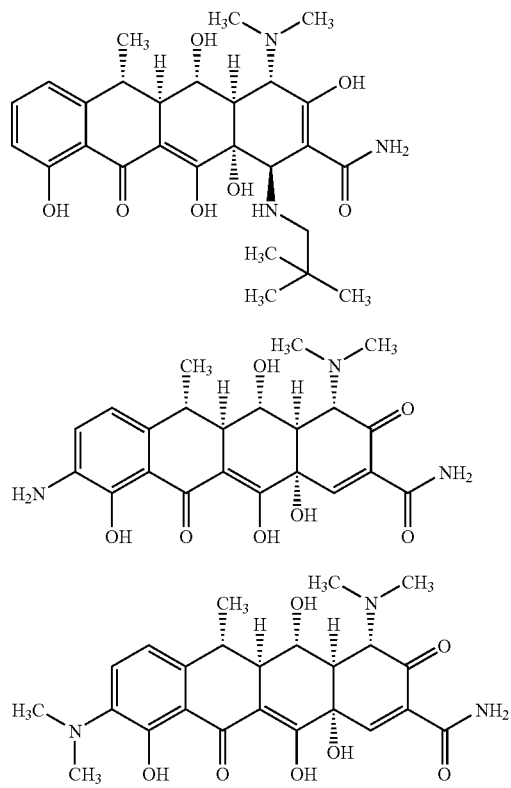

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:
1. A tetracycline compound of the formula (I)

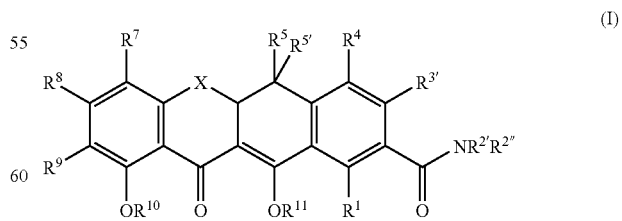

wherein
R$^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, heterocyclic, hydroxyl or halogen;

$R^{2'}$, $R^{2''}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$ and $R^{11}$ are each independently hydrogen, alkyl, aryl, benzyl, arylalkyl or a pro-drug moiety;

$R^{3'}$ is hydroxyl, alkoxy, arylalkyloxy, hydrogen or a prodrug moiety;

$R^4$ is $NR^{4a}R^{4b}$, alkyl, alkenyl, alkynyl, hydroxyl or halogen;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;

$R^6$ and $R^{6'}$ are each hydrogen;

$R^7$ is hydroxyl, substituted alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso or $-(CH_2)_{0-3}NR^{7c}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso or $-(CH_2)_{0-3}NR^{8c}C(=E')ER^{8a}$;

$R^9$ is hydrogen, hydroxyl, halogen, thiol, nitro, substituted alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso or $-(CH_2)_{0-3}NR^{9c}C(=Z')ZR^{9a}$;

$R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

E is $CR^{8d}R^{8e}$, S, $NR^{8b}$ or O;

E' is O, $NR^{8f}$ or S;

W is $CR^{7d}R^{7e}$, S, $NR^{7b}$ or O;

W' is O, $NR^{7f}$ or S;

X is $CR^6R^6$;

Z is $CR^{9d}R^{9e}$, S, $NR^{9b}$ or O; and

Z' is O, S or $NR^{9f}$, and pharmaceutically acceptable salts, esters and enantiomers thereof.

2. The tetracycline compound of claim 1, wherein $R^{2'}$, $R^{3'}$, $R^{10}$ and $R^{11}$ are each hydrogen or a prodrug moiety; $R^4$ is $NR^{4a}R^{4b}$; $R^{4a}$ and $R^{4b}$ are each alkyl; and $R^{2''}$, $R^5$ and $R^{5'}$ are each hydrogen.

3. The tetracycline compound of claim 1, wherein it $R^4$ is $NR^{4a}R^{4b}$; $R^{4a}$ and $R^{4b}$ are each alkyl; it $R^5$ is hydroxyl and $R^{5'}$ is hydrogen.

4. The tetracycline compound of claim 1, wherein it $R^4$ is $NR^{4a}R^{4b}$; $R^{4a}$ and $R^{4b}$ are each alkyl; $R^5$ and $R^{5'}$ are hydrogen atoms and $R^7$ is dimethylamino.

5. The tetracycline compound of claim 1, wherein $R^9$ is hydrogen.

6. The tetracycline compound of claim 1, wherein $R^9$ is substituted or unsubstituted aryl.

7. The tetracycline compound of claim 6, wherein $R^9$ is substituted or unsubstituted phenyl.

8. The tetracycline compound of claim 6, wherein $R^9$ is substituted or unsubstituted heteroaryl.

9. The tetracycline compound of claim 1, wherein $R^9$ is substituted alkyl.

10. The tetracycline compound of claim 9, wherein $R^9$ is aminoalkyl.

11. The tetracycline compound of claim 10, wherein $R^9$ is aminomethyl.

12. The tetracycline compound of claim 11, wherein $R^9$ is alkylaminomethyl.

13. The tetracycline compound of claim 1, wherein $R^9$ is substituted or unsubstituted amino.

14. The tetracycline compound of claim 1, wherein $R^9$ is nitro or halogen.

15. The tetracycline compound of claim 1, wherein $R^7$ is substituted or unsubstituted aryl.

16. The tetracycline compound of claim 1, wherein $R^7$ is substituted alkyl.

17. The tetracycline compound of claim 16, wherein $R^7$ is aminoalkyl.

18. The tetracycline compound of claim 17, wherein $R^7$ is aminomethyl.

19. The tetracycline compound of claim 18, wherein $R^7$ is alkylaminomethyl.

20. The tetracycline compound of claim 1, wherein $R^7$ is substituted or unsubstituted amino.

21. The tetracycline compound of claim 1, wherein $R^8$ is hydrogen.

22. The tetracycline compound of claim 1, wherein $R^{3'}$ is hydrogen, hydroxyl or alkoxy.

23. The tetracycline compound of claim 1, wherein $R^{10}$ is hydrogen, alkyl, aryl or arylalkyl.

24. The tetracycline compound of claim 1, wherein $R^{11}$ is hydrogen, alkyl, aryl or arylalkyl.

25. The tetracycline compound of claim 1, wherein $R^1$ is hydrogen, halogen, hydroxyl, thiol, alkoxy or amino.

26. The tetracycline compound of claim 1, wherein $R^1$ is alkyl, alkenyl, alkynyl or aryl.

27. The tetracycline compound of claim 1, wherein said tetracycline compound is:

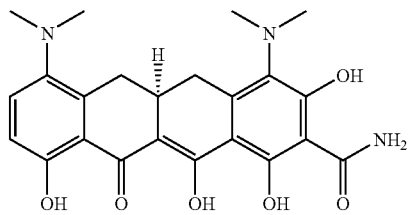

or

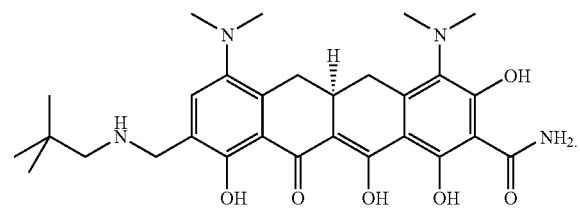

28. A pharmaceutical composition comprising an effective amount of a tetracycline compound and a pharmaceutically acceptable carrier, wherein said tetracycline compound is a compound of claim 1.

29. A tetracycline compound of the formula (I)

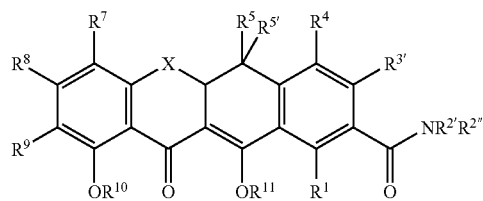

wherein
- $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, heterocyclic, hydroxyl or halogen;
- $R^{2'}$, $R^{2''}$, $R^{4a}$ and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{10}$ and $R^{11}$ are each independently hydrogen, alkyl, aryl, benzyl, arylalkyl or a pro-drug moiety;
- $R^{3'}$ is hydroxyl, alkoxy, arylalkyloxy, hydrogen or a prodrug moiety;
- $R^{4'}$ alkyl, alkenyl, alkynyl, hydroxyl or halogen;
- $R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy or aryl carbonyloxy;
- $R^6$ and $R^{6'}$ are each hydrogen;
- $R^7$ is hydrogen, halogen, thiol or nitro;
- $R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso or —$(CH_2)_{0-3}NR^{8c}C(=E')ER^{8a}$;
- $R^9$ is hydroxyl, substituted alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso or —$(CH_2)_{0-3}NR^{9c}C(=Z')ZR^{9a}$;
- $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, $R^{9f}$, are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- E is $CR^{8d}R^{8e}$, S, $NR^{8b}$ or O;
- E' is O, $NR^{8f}$ or S;
- X is $CR^{6'}R^6$;
- Z is $CR^{9d}R^{9e}$, S, $NR^{9b}$ or O;
- Z' is O, S or $NR^{9f}$, and pharmaceutically acceptable salts, esters and enantiomers thereof.

30. The tetracycline compound of claim 29, wherein $R^{2'}$, $R^{3'}$, $R^{10}$ and $R^{11}$ are each hydrogen or a prodrug moiety; $R^4$ is $NR^{4a}R^{4b}$; $R^{4a}$ and $R^{4b}$ are each alkyl; and $R^{2''}$, $R^5$ and $R^{5'}$ are each hydrogen.

31. The tetracycline compound of claim 29, wherein $R^4$ is $NR^{4a}R^{4b}$; $R^{4a}$ and $R^{4b}$ are each alkyl; $R^5$ is hydroxyl and $R^{5'}$ is hydrogen.

32. The tetracycline compound of claim 29, wherein $R^9$ is substituted or unsubstituted aryl.

33. The tetracycline compound of claim 32, wherein $R^9$ is substituted or unsubstituted phenyl.

34. The tetracycline compound of claim 32, wherein $R^9$ is substituted or unsubstituted heteroaryl.

35. The tetracycline compound of claim 29, wherein $R^9$ is substituted alkyl.

36. The tetracycline compound of claim 29, wherein $R^9$ is substituted or unsubstituted amino.

37. The tetracycline compound of claim 29, wherein $R^7$ is hydrogen.

38. The tetracycline compound of claim 29, wherein $R^7$ is nitro or halogen.

* * * * *